US007491403B2

(12) United States Patent
Borodic

(10) Patent No.: US 7,491,403 B2
(45) Date of Patent: Feb. 17, 2009

(54) **PHARMACEUTICAL *BOTULINUM* TOXIN COMPOSITIONS**

(75) Inventor: Gary Borodic, Canton, MA (US)

(73) Assignee: Botulinum Toxin Research Associates, Quincy, MA (US)

( * ) Notice: Subject to any disclaimer, the term of this patent is extended or adjusted under 35 U.S.C. 154(b) by 0 days.

(21) Appl. No.: 10/740,755

(22) Filed: Dec. 22, 2003

(65) Prior Publication Data

US 2004/0151741 A1      Aug. 5, 2004

Related U.S. Application Data

(60) Provisional application No. 60/435,901, filed on Dec. 20, 2002.

(51) Int. Cl.
*A61K 39/08*     (2006.01)
*A61K 38/38*     (2006.01)

(52) U.S. Cl. .................. 424/239.1; 514/12; 424/184.1; 424/234.1; 424/247.1

(58) Field of Classification Search .............. 424/239.1, 424/184.1, 94.5, 234.1, 247.1, 94.1; 514/12; 530/350, 324, 325, 327, 328, 329, 337
See application file for complete search history.

(56) References Cited

U.S. PATENT DOCUMENTS

| 4,845,042 | A | * | 7/1989 | Newman et al. ............. 436/545 |
| 4,861,627 | A | | 8/1989 | Mathiowitz et al. |
| 5,053,005 | A | * | 10/1991 | Borodic ....................... 604/511 |
| 5,069,936 | A | | 12/1991 | Yen et al. |
| 5,437,291 | A | * | 8/1995 | Pasricha et al. ............. 128/898 |
| 5,512,547 | A | * | 4/1996 | Johnson et al. ................ 514/21 |
| 5,562,907 | A | * | 10/1996 | Arnon ....................... 424/236.1 |
| 5,576,468 | A | | 11/1996 | Lubowitz |
| 5,696,077 | A | * | 12/1997 | Johnson et al. ................. 514/2 |
| 5,756,468 | A | * | 5/1998 | Johnson et al. ................ 514/21 |
| 5,846,929 | A | | 12/1998 | Johnson et al. |
| 5,939,070 | A | | 8/1999 | Johnson et al. |
| 5,965,699 | A | * | 10/1999 | Schmidt et al. ............. 530/326 |
| 5,989,545 | A | | 11/1999 | Foster et al. |
| 6,051,239 | A | * | 4/2000 | Simpson et al. ........... 424/239.1 |
| 6,087,327 | A | * | 7/2000 | Pearce et al. .................... 514/2 |
| 6,100,306 | A | | 8/2000 | Li et al. |
| 6,203,794 | B1 | | 3/2001 | Dolly et al. |
| 6,210,707 | B1 | | 4/2001 | Papahadjopoulos et al. |
| 6,214,602 | B1 | * | 4/2001 | Zdanovsky ............... 435/252.3 |
| 6,306,423 | B1 | * | 10/2001 | Donovan et al. ............ 424/423 |
| 6,312,706 | B1 | | 11/2001 | Lai et al. |
| 6,312,708 | B1 | | 11/2001 | Donovan |
| 6,383,509 | B1 | | 5/2002 | Donovan et al. |
| 6,429,189 | B1 | | 8/2002 | Borodic |
| 6,447,787 | B1 | * | 9/2002 | Gassner et al. ............ 424/247.1 |
| 6,545,126 | B1 | * | 4/2003 | Johnson et al. ............. 530/350 |
| 6,579,847 | B1 | * | 6/2003 | Unger ............................ 514/2 |
| 6,585,993 | B2 | | 7/2003 | Donovan et al. |
| 6,620,617 | B2 | | 9/2003 | Mathiowitz et al. |
| 7,140,371 | B2 | * | 11/2006 | Hanin et al. ................. 128/898 |
| 7,211,261 | B1 | * | 5/2007 | Moyer et al. ............. 424/236.1 |
| 2001/0043930 | A1 | | 11/2001 | Aoki et al. |
| 2002/0064536 | A1 | * | 5/2002 | Hunt ....................... 424/247.1 |
| 2002/0107199 | A1 | | 8/2002 | Walker |
| 2003/0086899 | A1 | * | 5/2003 | Jarari ....................... 424/78.31 |
| 2003/0108597 | A1 | * | 6/2003 | Chancellor et al. .......... 424/450 |
| 2003/0118598 | A1 | * | 6/2003 | Hunt ....................... 424/184.1 |
| 2003/0138437 | A1 | | 7/2003 | Hunt |
| 2003/0138460 | A1 | * | 7/2003 | Hunt ....................... 424/239.1 |
| 2004/0037853 | A1 | * | 2/2004 | Borodic ................... 424/239.1 |
| 2004/0071735 | A1 | * | 4/2004 | Marchini et al. .......... 424/239.1 |
| 2004/0082540 | A1 | * | 4/2004 | Hermida Ochoa ........... 514/54 |
| 2004/0126396 | A1 | | 7/2004 | Aoki et al. |
| 2004/0151741 | A1 | * | 8/2004 | Borodic ................... 424/239.1 |
| 2004/0175400 | A1 | * | 9/2004 | Borodic ................... 424/239.1 |
| 2004/0247606 | A1 | * | 12/2004 | Borodic et al. ........... 424/184.1 |
| 2005/0031648 | A1 | * | 2/2005 | Brin et al. ................ 424/239.1 |
| 2005/0112146 | A1 | * | 5/2005 | Graham ................... 424/239.1 |

(Continued)

FOREIGN PATENT DOCUMENTS

EP      0593176 A2 *  9/1993

(Continued)

OTHER PUBLICATIONS

Epinephrine package insert #58-6165, Abbott Laboratories, pp. 1-5, May 2000.*
Botox package insert Allergan Pharmaceuticals, pp. 1-4.*
Schmidt, James J. et al, Journal of Protein Chemistry, vol. 16(10), 1997, Endoproteinase activity of type A botulinum neurotoxin: substrate requirements and activation by serum albumin.*
Gill, Michael, D, Microbiological Reviews, Mar. 1982, vol. 46(1) pp. 86-94, Bacterial toxins: a table of lethal amounts.*
Goodnough, MC et al, Applied and Environmental Microbiology, Oct. 1992, vol. 58(10), pp. 3426-3428, Stabilization of botulinum toxin type A during lyophilization.*

(Continued)

*Primary Examiner*—Mark Navarro
*Assistant Examiner*—Ginny Portner
(74) *Attorney, Agent, or Firm*—Milbank, Tweed, Hadly & McLoy LLP

(57) ABSTRACT

*Botulinum* toxin, a well know systemic poison, produces favorable therapeutic effect by virtue of regionally attaching to nerves within the myoneural junction and possibly other tissues in a target region of a particular tissue. The present invention provides compositions of *botulinum* toxin and a sequestration agent that increase sequestration and delivery of the *botulinum* toxin to neural and associated tissues, as compared with available formulations of *botulinum* toxins, and thereby produce a beneficial clinical effect. The sequestration agents of the present invention include proteins, lipids and carbohydrates. A preferred composition of the present invention comprises a *botulinum* toxin and an albumin. The present invention also provides methods of treating neuromuscular diseases and pain using the disclosed compositions and methods of making the disclosed compositions.

55 Claims, No Drawings

U.S. PATENT DOCUMENTS

| | | | |
|---|---|---|---|
| 2005/0142150 A1* | 6/2005 | Graham | 424/239.1 |
| 2005/0208075 A1* | 9/2005 | Borodic | 424/239.1 |
| 2005/0208076 A1* | 9/2005 | Hunt | 424/239.1 |
| 2005/0214326 A1* | 9/2005 | Hunt | 424/239.1 |
| 2005/0238663 A1* | 10/2005 | Hunt | 424/239.1 |
| 2005/0238664 A1* | 10/2005 | Hunt | 424/239.1 |
| 2005/0238667 A1* | 10/2005 | Hunt | 424/239.1 |
| 2006/0147471 A1* | 7/2006 | Borodic et al. | 424/239.1 |
| 2006/0269575 A1* | 11/2006 | Hunt | 424/239.1 |
| 2007/0020294 A1* | 1/2007 | Marchini et al. | 424/239.1 |
| 2007/0026019 A1* | 2/2007 | Hunt | 424/239.1 |

FOREIGN PATENT DOCUMENTS

| | | | |
|---|---|---|---|
| WO | 94/00481 | * | 1/1994 |
| WO | WO 94/00481 | | 1/1994 |
| WO | 96/39166 | * | 12/1996 |
| WO | WO 96/39166 | | 12/1996 |
| WO | 97/35604 | * | 10/1997 |
| WO | WO 97/35604 | | 10/1997 |
| WO | 00/24419 | * | 5/2000 |
| WO | 01/58472 | * | 8/2001 |
| WO | WO 01/58472 A2 | | 8/2001 |
| WO | 03/041724 | * | 5/2003 |
| WO | WO 2004/060384 A2 | | 7/2004 |

OTHER PUBLICATIONS

Schmidt, James J. et al, J. Pro. Chem., vol. 16(1), 1997, pp. 19-26.*
Kalandakanond, Sarinee et al, 2001, The Journal of Pharmacology and Experimental Therapeutics, vol. 296(3), pp. 749-755.*
Borodic, "Botulinum A Toxin for (expressionistic) ptosis overcorrection after frontalis sling," Ophtalmic Plastic & Recostructive Surg. 8(2): 137-142, (1992).
Borodic et al. Botulinum A Toxin for the treatment of spasmodic torticollis, Dysphagia and Regional Toxin Spread. Head & Neck, 12: 392-398 (1990).
Nussgens et al. "Comparison of two botulinum-toxin preparations in the treatment of essential blepharospasm," Graefes Arch Clin Exp Ophthalmol 235(4): 197-199 (1997).
Bigalke et al. Botulinum A Toxin: DYSPORT improvement of biological availability,: Exp. Neurol. 168(1): 162-170 (2001).
Lew et al. "Botulinum toxin type B: a double-blind, placebo-controlled, safety and efficacy study in cervical dystonia," Neurology 49(3): 701-707 (1997).
Borodic et al "Botulinum Toxin: Clinical and Scientific Aspects." Ophthalmology Clinics of North America 4: 491-503 (1991).
Borodic et al "Botulinum: a toxin for spasmodic torticollis, multiple vs. single point injections per muscle," Head and Neck 14:33-37 (1992).
Ranoux et al "Respective potencies of Dysport and Botox: a double blind, randomized, crossover study in cervical dystonia," J. Neuro. Neurosurg. Psychiatry 72: 459-462 (2002).
Holck et al "Comparison of High Dose Botulinum Toxin Type B to Botulinum Type A in the Treatment of Lateral Rhylids," American Society of Ophthalmic Plastic and Reconstructive Surgeons Annual Meeting, Anaheim, CA Nov. 14, 2003).
Borodic et al "Botulinum B Toxin as an Alternative to Botulinum A Toxin, A Histologic study," Ophthalmic Plastic and Reconstructive Surgery 9(3): 182-190 (1993).
Borodic et al. "Botulinum A Toxin for Treatment of Aberrant Facial Nerve Regeneration," Plastic and Reconstructive Surger, 91(6): 1042-1045, 1993.
Troll, Gabriele, et al., "Diplopia After Cataract Surgery Using Forty Percent Lidocaine in the Absence of Wydase (Sodium Hyaluronidase)", J. Clin. Anesth. vol. 11, Nov. 1999, pp. 615-616.
International Search Report and Written Opinion for PCT/US2006/015459 dated Mar. 1, 2007.
Borodic et al. "Botulinum toxin theraphy, immunologic resistance, and problems with available materials," Neurology 1996; 46:26-29.
Schantz, Edward J. et al. Standardized Assay for Clostridium boutilum Toxins, Journal of the AOAC, vol. 61, No. 1, 1978.
Rollnik, J. et al., "Low-Dose Treatment of Cervical Dystonia, Blepharospasm and Facial Hemispasm with Albumin-Diluted Botulinum Toxin Type A Under EMG Guidance", Eur Neurol 2000; 43:9-12.
Goodnough, M. et al., "Stabilization of Botulinum Toxin Type A during Lyophilization," Allied and Environmental Microbiologu, Oct. 1992, p. 3426-3428.
Gassner, H. et al., "Addition of an Anesthetic Agent to Enhance the Predictability of the Effects of Botulinum Toxin Type A Injections: A Randomized Controlled Study", Mayo Clin Proc, Jul. 2000, vol. 75.
Johnson, M. et al., "The Use of a Water-Soluble Carbodiimide as a Coupling Reagent in the Passive Hemagglutination Test", The Journal of Immunology, vol. 97, No. 6.
Langhein, C. et al., "Antiobody response to bacterial antigens covalently bound to biodegradable polymerized serum albumin beads", Journal of Applied Bacteriology 1987, 63, 443-448.
International Search Report for PCT No. PCT/IB03/06145 dated Aug. 11, 2005.
Rollnik, Jens D., et al., "Low-Dose Treatment of Cervical Dystonia, Blepharospasm and Facial Hemispasm with Albumin-Diluted Botulinum Toxin Type A under EMG Guidance", European Neurology vol. 43, 2000, pp. 9-12.
Communication pursuant to Article 96(2) EPC for 03 814 518. 1—2107 dated Sep. 4, 2006.
Bigalke, Hans et al., "Botulinum A Toxin: Dysport Improvement of Biological Availability", Experimental Neurology 168, 162-170 (2001).

* cited by examiner

PHARMACEUTICAL *BOTULINUM* TOXIN COMPOSITIONS

This application claims benefit to U. S. Provisional Application Ser. No. 60/435,901 that was filed on Dec. 20, 2002.

TECHNICAL FIELD OF THE INVENTION

This invention relates to improved pharmaceutical compositions comprising *botulinum* neurotoxin and a sequestration agent. The invention further provides pharmaceutical compositions and methods for the treatment of a variety of neuromuscular diseases.

BACKGROUND OF THE INVENTION

*botulinum* neurotoxin is a toxin isolated from a strain of *Clostridium botulinum,* that acts at the neuromuscular junction by inhibiting release of acetylcholine. *botulinum* toxin is initially formed as a single-chain polypeptide that is cleaved to form a light chain that is bound to a heavy chain through a disulfide bond. The denervating effect of *botulinum* toxin occurs through: 1) the binding of the heavy chain to high-affinity receptors at the presynaptic terminal; 2) internalization of *botulinum* toxin through endocytosis; 3) translocation of the light chain into the cytoplasm of the nerve terminal; and 4) the endo metalloprotease activity of the light chain (zinc is a cofactor) cleaves specific synaptic proteins that inhibit fusion of synaptic vesicles with the presynaptic membrane, thereby inhibiting the release of acetylcholine contained in the vesicles. Absent acetylcholine, the muscle does not receive the necessary signal for the muscle to contract.

Although a deadly toxin at higher concentrations and quantities, *botulinum* toxin has been used as a valuable therapeutic for the treatment of many neuromuscular diseases (e.g., dystonia, hemifacial spasm, bruxism, spasticity, cerebral palsy, torticollis), as well as sensory disorders and cutaneous disorders (myofascial pain, migraine, tension headaches, neuropathy, hyperhydrosis). Prior to this invention, the in vivo binding of albumin to *botulinum* toxin has never been identified as important to clinical effectiveness of *botulinum*-toxin-based pharmaceuticals. By enhancing regional sequestration of the neurotoxin and facilitating saturation of neurotoxin receptors on neural tissues, high-concentration-albumin formulations improve the clinical effectiveness of *botulinum* toxin and reduce side effects such as those resulting from diffusion of the *botulinum* toxin from the site of administration. There has been no prior suggestion that altering the formulation of *botulinum* toxin by increasing its concentration relative to the neurotoxin could enhance the effectiveness for the treatment of human disease. The existing *botulinum* toxin preparations currently available for clinical practice are BOTOX®, DYSPORT®, MYOBLOC®. The present invention identifies the mechanism and provides compositions of improved utility of *botulinum*-toxin-based pharmaceuticals by increasing the concentration of a sequestration agent and other viscous agents to enhance sequestration and improve the effectiveness where other available *botulinum* toxin preparations have failed.

In recent years, Borodic et al. have characterized the regional effect of *botulinum* toxin using muscle fiber morhphometrics, cholinesterase staining, and cutaneous wrinkling from depression of facial muscle tone. (Borodic (1992) *botulinum* A toxin for (expressionistic) ptosis overcorrection after frontalis sling. *Ophthalmic Plastic and Reconstructive Surg.* 8(2): 137-142; incorporated herein by reference in its entirety).

Since its introduction as a therapeutic agent, the pharmaeutical measurement of the denervating or biologic activity of *botulinum* toxin has been the $LD_{50}$ unit using a 18-22 gram Swiss-Webster mouse, quantitated statistically by injecting cohorts of mice at different dilutions from the purified *botulinum* neurotoxin protein and its protein complexes. This measurement has the advantage of simplicity of a clear endpoint determination (living or dead mouse), however the $LD_{50}$ unit does not predict clinical behavior of various *botulinum* toxin formulations when compared in clinical studies. For instance, one preparation of type B *botulinum* toxin (MYOBLOC®) requires 5,000-15,000 $LD_{50}$ units to treat torticollis whereas another preparation of *botulinum* toxin Type A (BOTOX®) requires only 100-300 $LD_{50}$ units. Similarly, the $LD_{50}$ unit has failed to distinguish differences in therapeutic behavior of different sources of the same *botulinum* toxin immunotype. For instance, approximately 50-300 units of BOTOX® is required to treat blepharospasm and cervical dystonia compared to 200-1200 units of DYSPORT®, another preparation of *botulinum* type A toxin. Table 1 illustrates the varying doses for different diseases.

TABLE 1

Dosing comparisons between various pharmaceutical formulations of botulinum toxin.

| Formulation | Essential Blepharospasm | Torticollis |
| --- | --- | --- |
| BOTOX ® | 50 U[1] | 200 U |
| DYSPORT ® | 200 U | 600-1,200 U |
| MYOBLOC ® | 3,000-5,000 U | 10,000-15,000 U |

[1]Units (U) are $LD_{50}$ units determined using 20-30 g Swiss-Webster mice, as described herein.

A. Complications Associated with Conventional *botulinum*-Toxin Formulations.

Beyond effective dose requirements, substantial differences in the complication rate have been noted at therapeutic quantities of different *botulinum* preparations. Side effects such as those resulting from diffusion of the *botulinum* toxin from the site of administration appear to be dependent on the formulation of *botulinum* toxin. For instance, dysphagia rates (difficulty swallowing) is a well-known complication of *botulinum* toxin administration when used for the treatment of cervical dystonia. (Borodic et al. (1990) *Botulinum* A toxin for the treatment of spasmodic torticollis. *Dysphagia and Regional Toxin Spread. Head & Neck,* 12: 392-398; incorporated herein by reference in its entirety). Differences in the rate of this complication between formulations has been well appreciated when reviewing prior art literature between 1984-1995. Furthermore differences in the rate of ptosis have been reported when comparing various immunotypes and different preparations of the same immunotype (see Table 1). It has become well accepted that this complication is the result of diffusion of *botulinum* toxin away from the injections sites, a property which is in conflict with the clinical goal of containing the denervating or biologic effect to a specific target region.

TABLE 2

Diffusion-related complications between various pharmaceutical formulations of botulinum toxin.

| Complication | BOTOX ® | DYSPORT ®[2] | MYOBLOC ®[3] |
| --- | --- | --- | --- |
| Ptosis[1] | <2% | 12-15% | 30-40% |
| Dysphagia | <2% | 14-21% | 10-17% |

[1]Nussgens et al. (1997) Comparison of two botulinum-toxin preparations in the treatment of essential blepharospasm. Graefes Arch Clin Exp Ophthalmol 235(4): 197-199.
[2]Phase 3 Studies 1998-1989 for Oculinum Meta-analysis of clinical studies on Dysphagia and Botulinum 1995 at NIH (Borodic).
[3]Lew et al. (1997) Botulinum toxin type B: a double-blind, placebo-controlled, safety and efficacy study in cervical dystonia. Neurology 49(3): 701-707.

In 1991, Borodic et al. demonstrated a histologic model demonstrating a histochemical and morphologic diffusion gradient from point injections of *botulinum* toxin. (Borodic et al. (1991) *botulinum* toxin: Clinical and scientific aspects. *Opthamology Clinics of North America* 4: 491-503; incorporated herein by reference in its entirety). The gradient was further demonstrated to be dose dependent over single muscle strips and capable of crossing fascial planes. The diffusion model was further demonstrated on the facial wrinkling pattern of the human forehead. (Borodic et al (1992) *botulinum* toxin for spasmodic torticollis, multiple vs single point injections per muscle. *Head and Neck* 14: 33-37). Diffusion was thereafter used to explain the mechanism for dysphagia after surface injections of *botulinum* injection for the human neck and ptosis (drooping eyelid complication) after periocular injections for the treatment of essential blepharopasm. Ptosis results from diffusion of neuromuscular blocking activity from the lid edge to the muscular portion of the upper eyelid retractor, which lies in the upper orbital space. Dysphagia results from diffusion of neuromuscular weakening effect from the sternomastoid muscle, targeted for treatment of torticllolis, to peripharygeal musculature which generates the force for effective swallowing. From both histologic models and clinical experience, diffusion appears to be directly related to the quantity of toxin given in $LD_{50}$ units, that is, the greater the $LD_{50}$ units used, the greater the diffusion from a point injection. From literature summary from the 1980's and early 1990's, dysphagia is more common with use of DYSPORT® than BOTOX® at effective doses. Recently, from studies done at European centers, the differences in dysphagia rates have been confirmed (Ranoux et al. (2002) Respective potencies of DYSPORT® and BOTOX®: a double blind, randomized, crossover study in cervical dystonia. *J. Neurol. Neurosurg. Psychiary* 72: 459-462). Differences in ptosis rates for the treatment of blepharospasm have also been observed comparing BOTOX® with DYSPORT® with BOTOX® demonstrating less common incidence of this complication (Nussgens et al. (1997) Comparison of two *botulinum*-toxin preparations in the treatment of essential Blepharospasm. *Graefes Arch Clin Exp Ophthalmol*. 235(4): 197-199). Major differences in the ptosis complication have been reported when using *botulinum* toxin type B for the treatment of glabellar and forehead wrinkles when compared to *botulinum* type A (BOTOX®). (Holck et al. Comparison of High Dose *botulinum* Toxin Type B to *botulinum* Type A in the Treatment of Lateral Canthal Rhytids American Society of Ophthalmic Plastic and reconstructive Surgeons Annual Meeting, Anaheim, Calif. Nov. 14, 2003).

B. Sequestration.

Albumin was initially used to formulate *botulinum* toxin based pharmaceuticals because of its stabilizing effect on the biologic activity of the neurotoxin at high dilutions (see Schantz, *Botulinum* Toxin Therapy, Marcel Dekker 1994). Dilution of the purified *botulinum* toxin crystals with physiologic saline or water would cause the biologic activity and pharmaceutical properties to be lost at high dilutions. Additionally, the albumin has been reported to help keep the neurotoxin molecule from binding to glass containers. During the pre-clinical development of BOTOX® or any other *botulinum* toxin prepared for pharmaceutical use, there was no appreciation for the importance of albumin in the formulation other than a dilution stabilizer and excipient to keep the neurotoxin from binding to glass.

BOTOX® and DYSPORT® are derived from different strains of Clostridial species. BOTOX® is derived from the Hall strain of *Clostridium botulinum* originally maintained by the University of Wisconsin, whereas DYSPORT® is derived from British Microbiology Collection. Immunologic cross reactivity exists between the products as both products were derived from immunotype A strains. Despite similar immuotypes, the clinical responses between BOTOX® and DYSPORT® may be explained by the differences in the excipients used in each formulation. The difference in human serum albumin concentrations between BOTOX® and DYSPORT® are outlined in Table 3.

TABLE 3

Human Serum Albumin content of various pharmaceutical formulations of botulinum toxin.

| Formulation | Albumin[1] | $LD_{50}$/µg albumin |
| --- | --- | --- |
| BOTOX ® | 500 µg | 0.2 |
| DYSPORT ® | 125 µg | 5.0 |

[1]Albumin is represented in mg per 100 $LD_{50}$ units of botulinum toxin. Other differences exist including the presence of stabilizing sugars, Lactose is used in DYSPORT ® and not used in BOTOX ®.

The albumin discrepancy between BOTOX® and DYSPORT® is almost identical to the difference in dose requirements observed between BOTOX® and DYSPORT® in multiple clinical studies. The corrolation between the albumin ratio/clinical potency ratio is further strengthened by changes in pharamcologic properties of DYSPORT® when albumin is added to the vials using a mouse hemidiaphram animal model. Wohlfahrt et al. noted using this model that adding albumin to one vials of DYSPORT® brought biologic activity higher using the mouse hemi-diaphragm model. (Biglalke et al (2001) *Botulinum* A toxin: DYSPORT® improvement of biological availability. *Exp. Neurol.* 168(1): 162-170). The authors suggested the increased biologic activity resulted from increased stability as measured with the mouse $LD_{50}$ bioassay afforded by the albumin concentration increase. (Biglalke et al (2001) *Botulinum* A toxin: DYSPORT® improvement of biological availability. *Exp. Neurol.* 168(1): 162-170). The authors explained the differences of albumin on the $LD_{50}$ bioassay without reference to mechanism of action in tissues or pharmacolgic-pharmacokinetic importance, that is, in vivo albumin binding, enhanced sequestration, and improvement in therapeutic effects. The same authors further observed in a rat-diaphragm preparation, that the addition of albumin to the BOTOX® preparation could not substantially increase regional denervative effects and did not advocate any changes in formulation. The findings of these researchers concluded that there was an effect of the albumin concentration on the $LD_{50}$ measurements however, there work did not demonstrate any increased potency of BOTOX® on regional denervation or that DYSPORT® could be enhance to give any greater denervation potency over BOTOX®. There work was limited by the in vitro nature of their experiments, that is, using a non blood perfused animal dissection of a motor nerve (phrenic nerve) and diaphragm muscle, which fails to accounts for dilutions and tissue fluid flow capable of washing injected toxin away from targeted tissue prior to binding with the nerve axon terminal receptors. The real time application requires an in vivo analysis of the effects of albumin on regional denervation as outlined in the following experiments. Their work did identify reasons for differences in $LD_{50}$ as measured by the mouse lethality assay. The conclusion were no improvements in potency or effectiveness could be made over existing BOTOX® preparation and is directly contrary to the conclusion derived herein. (Hanover Germany International *Botulinum* Toxin Meeting 2002).

Differences in potency, issues relating diffusion and containment of the biologic effect are important in the pharmacology of *botulinum*-based pharmaceuticals. Described herein is a method for altering compositions of *botulinum* based pharmaceuticals to enhance potency, increase sequestration of the *botulinum* toxin and limit adverse effects of *botulinum*-based pharmaceuticals.

SUMMARY OF THE INVENTION

The present invention provides a composition comprising *botulinum* toxin and a sequestration agent for use in treating various neuromuscular diseases and localized denervation. In one embodiment, the sequestration agent is present in an amount between 550 and 550,000 µg sequestration agent per 100 $LD_{50}$ units *botulinum* toxin. In another embodiment, the sequestration agent is present in an amount between 550 and 5,500 µg sequestration agent per 100 $LD_{50}$ units *botulinum* toxin. In a further embodiment, the sequestration agent is present in an amount between 5,500 and 13,000 µg sequestration agent per 100 $LD_{50}$ units *botulinum* toxin. In a preferred embodiment, the sequestration agent is present in an amount between 13,000 and 50,500 µg sequestration agent per 100 $LD_{50}$ units *botulinum* toxin. In a more preferred embodiment, the sequestration agent is present in an amount between 50,500 and 505,000 µg sequestration agent per 100 $LD_{50}$ units *botulinum* toxin. In the most preferred embodiment, the sequestration agent is formulated as encapsulated microspheres in an amount between 50,500 and 90,500 µg sequestration agent per 100 $LD_{50}$ units *botulinum* toxin.

The *botulinum* toxin of the present compositions may be selected from a variety of strains of *Clostridium botulinum*. In a preferred embodiment, the compositions of the present invention comprises a *botulinum* toxin selected from the group consisting of *botulinum* toxin types A, B, C, D, E, F and G. In a preferred embodiment, the *botulinum* toxin is *botulinum* toxin type A. In a more preferred embodiment, the *botulinum* toxin is *botulinum* toxin type A from the Hall strain of *Clostridium botulinum*.

In another embodiment, the compositions of the present invention comprise a *botulinum* toxin that consists essentially of fractionated-light-chain *botulinum* toxin. In yet another embiodment, the *botulinum* toxin consists essentially of a mixture of hybrid and chain-translocated forms of *botulinum* toxin . In a further embodiment, the *botulinum* toxin consists essentially of chimeric forms of *botulinum* toxin. Although the present invention may utilize any *botulinum* toxin, *botulinum* toxin fragment that retains neurotoxic activity, *botulinum* toxin chimeras and hybrids, chemically-modified *botulinum* toxin, and specific activities well known to those of ordinary skill in the art, in one embodiment the *botulinum* toxin is purified to a specific activity greater than or equal to 20 $LD_{50}$ units per nanogram *botulinum* toxin.

The present invention provides compositions of *botulinum* toxin and a sequestration agent wherein the ratio of $LD_{50}$ units of *botulinum* toxin to µg sequestration agent is less than or equal to 0.2 for *botulinum* toxin type A and is less than or equal to 10 for *botulinum* toxin type B.

Each composition of the present invention, in addition to comprising a *botulinum* toxin and a sequestration agent, may further comprise a pharmaceutically acceptable carrier and/or zinc and/or a zinc salt. In one embodiment, the *botulinum* toxin is noncovalently bound to the asequestration agent. In another embodiment, the *botulinum* toxin is covalently bound to the sequestration agent.

The present invention provides compositions of a *botulinum* toxin and a sequestration agent, wherein the sequestration agent is selected from the group consisting of: proteins, lipids and carbohydrates. In a preferred embodiment, the sequestration agent is albumin, collagen, epinephrine or hyaluronate. In a more preferred embodiment, the sequestration agent is hyaluronate. In the most preferred embodiment, the sequestration agent is albumin.

The present invention further provides compositions comprising a *botulinum* toxin and a sequestration agent, wherein the sequestration agent is an albumin, preferably human serum albumin. Furthermore, in one embodiment, the albumin of the present compositions is recombinantly produced. In one embodiment, the albumin is present in an amount between 550 and 5,500 µg albumin per 100 $LD_{50}$ units *botulinum* toxin. In a further embodiment, albumin is present in an amount between 5,500 and 13,000 µg albumin per 100 $LD_{50}$ units *botulinum* toxin. In a preferred embodiment, albumin is present in an amount between 13,000 and 50,500 µg albumin per 100 $LD_{50}$ units *botulinum* toxin. In a more preferred embodiment, albumin is present in an amount between 50,500 and 505,000 µg albumin per 100 $LD_{50}$ units *botulinum* toxin. In a most preferred embodiment, albumin is formulated as encapsulated microspheres in an amount between 50,500 and 90,500 µg albumin per 100 $LD_{50}$ units *botulinum* toxin.

In another embodiment, the present invention provides a composition comprising *botulinum* toxin and a sequestration agent, wherein the sequestration agent is present in an amount between 550 and 900,500 µg sequestration agent per 100 $LD_{50}$ units *botulinum* toxin, wherein the albumin may be formulated as a solid albumin particle.

In one embodiment of the present invention, the compositions comprise a *botulinum* toxin and at least one seqestration agent. In a preferred embodiment, the compositions of the present invention comprising a *botulinum* toxin and albumin and further comprising one or more additional sequestration agents.

The present invention also provides methods of producing localized denervation in a subject in need thereof, comprising administering an effective amount of any of the compositions of the present invention that are described herein. In one embodiment, the methods of the present invention are used to produce denervation in a subject that suffers from a neuromuscular disease associated with increased muscle tone with involuntary movement. In another embodiment, the methods of the present invention are used to produce denervation in a subject that suffers from a neuromuscular disease. Preferably, the neuromuscular disease is characterized by increased muscle tone and/or involuntary movement, including but not limited to dystonias, spinal cord injury or disease, multiple sclerosis, spasticity, cerebral palsy, stroke, and the like. Preferably, the neuromuscular disease associated with increased muscle tone and/or involuntary movement is blepharospasm or torticollis. More preferably, the neuromuscular disease associated with increased muscle tone with involuntary movement is blepharospasm.

In one embodiment, the present invention provides methods for producing denervation in a subject suffering from blepharospasm comprising administering between 10-200 $LD_{50}$ units of a composition of the present invention, as described herein. In another embodiment, the present invention provides methods for producing denervation in a subject suffering from torticollis. Preferably, the effective amount of a composition of the present invention is between 10 and 3000 $LD_{50}$ units.

In another embodiment, the present invention provides a method of treating a condition selected from the group consisting of facial wrinkles, rhytides and cosmetic alteration of lip and brow, in a subject in need thereof, comprising administering an effective amount of a composition of the present invention, as disclosed herein. Preferably, the effective amount is between 2.5 and 400 $LD_{50}$ units.

In yet another embodiment, the present invention provides a method of treating human headache disorders in a subject in need thereof, comprising administering an effective amount of a composition of the present invention, as disclosed herein. Preferably, the effective amount is between 5 and 1000 $LD_{50}$ units.

In a further embodiment, the present invention provides a method of treating human migraine headache disorders in a subject in need thereof, comprising administering an effective amount of a composition of the present invention, as disclosed herein. Preferably, the effective amount is between 5 and 1,000 $LD_{50}$ units.

The present invention also provides a method of treating human inflammatory conditions in a subject in need thereof, comprising administering an effective amount of a composition of the present invention, as disclosed herein. Preferably, the effective amount is between 5 and 4,000 $LD_{50}$ units.

The present invention also provides a method of treating myopathic or neuropathic pain in a subject in need thereof, comprising administering an effective amount of a composition of the present invention, as disclosed herein. Preferably, the effective amount is between 5 and 4,000 $LD_{50}$ units.

The present invention also provides a method of treating back pain or arthritic pain in a subject in need thereof, comprising administering an effective amount of a composition of the present invention, as disclosed herein. Preferably, the effective amount is between 5 and 4,000 $LD_{50}$ units.

In yet another embodiment, the present invention provides a method of treating gastrointestinal spasm and strictures in a subject in need thereof, comprising administering an effective amount of a composition of the present invention, as disclosed herein. Preferably, the effective amount is between 5 and 4,000 $LD_{50}$ units.

The present invention provides a method of treating a hyperhyrosis syndrome in a subject in need thereof, comprising administering an effective amount of a composition of the present invention, as disclosed herein. Preferably, the effective amount is between 5 and 4,000 $LD_{50}$ units.

The present invention also provides a method of producing the compositions described herein. In one embodiment, the method comprises mixing a sequestration agent with botulinum toxin. In another embodiment, the method comprises freeze drying or flash drying a sequestration agent with botulinum toxin. Preferably, the botulinum toxin and the sequestration agent are in a weight to weight ratio which exceeds 100 μg sequestration agent to 1 ng of botulinum toxin.

DETAILED DESCRIPTION OF THE INVENTION

The present invention describes a method and composition to enhance the clinical effectiveness of botulinum-toxin preparation for clinical use by means of increasing sequestration of botulinum neurotoxin molecules in the region of the human or mammalian body targeted for therapy through the use of a sequestration agent or "molecular anchor". Enhanced sequestration using higher concentration of macromolecules such as proteins (e.g., albumin, collagen and the like), and/or lipids and/or polysaccharides (e.g., hyaluronate, and the like) can be useful to provide a molecular anchor to neurotoxin molecules preventing diffusion away from the injection point, causing maximal saturation of botulinum neurotoxin receptors, thereby achieving greater efficacy with the amount of neurotoxin used to achieve desired clinical effects. The sequestration agent enhances containment of regional denervation, and enhances clinical outcomes. The increased sequestration allows for better delivery to nerve ending, with enhanced uptake and augmentation of denervative and other biologic effects. The invention requires a sequestration agent added to a formulation of neurotoxin which binds to the neurotoxin, prevents dissemination of the neurotoxin and demonstrates improvement in clinical response in patients who were previously treated without the carrier molecule at preferred concentrations. The sequestration agent may be an existing excipient at significantly higher concentrations than previously used (such as human serum albumin), or a material that has not been previously used to stabilize botulinum toxin (such as sodium hyalumonate). The sequestration agent must bind to the botulinum toxin molecule and prevents its diffusion so that the neurotoxin may react with the nerve-terminal ending or any neural structure so that effectiveness of the therapy is improved.

A. Definitions.

As used herein, "Botulinum toxin" means a protein toxin and its complexes isolated from strains of Clostridium botulinum, including various immunotypes such as A,B,C1,C2, C3,D,E,Fand G.

As used herein, "an effective amount" is an amount sufficient to produce a therapeutic response. An effective amount may be determined with dose escalation studies in open-labeled clinical trials or bin studies with blinded trials.

As used herein "neuromuscular diseases" refer to any disease adversely affecting both nervous elements (brain, spinal cord, peripheral nerve) or muscle (striated or smooth muscle), including but not limited to involuntary movement disorders, dytonias, spinal cord injury or disease, multiple sclerosis, spasticity, cerebral palsy, and stroke.

As used herein, the term "neuromuscluar diseases" refer to any disease adversely affecting both nervous elements (brain, spinal cord, peripheral nerve) or muscle (striated or smooth muscle), including but not limited to involuntary movement disorders, dytonias, spinal cord injury or disease, multiple sclerosis, spasticity, cerebral palsy, and stroke.

As used herein, the term "pharmaceutically acceptable carrier" means a chemical composition, compound, or solvent with which an active ingredient may be combined and which, following the combination, can be used to administer the active ingredient to a subject. As used herein, "pharmaceutically acceptable carrier" includes, but is not limited to, one or more of the following: excipients; surface active agents; dispersing agents; inert diluents; granulating and disintegrating agents; binding agents; lubricating agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; antioxidants; stabilizing agents; and pharmaceutically acceptable polymeric or hydrophobic materials and other ingredients known in the art and described, for example in Genaro, ed., 1985, Remington's Pharmaceutical Sciences, Mack Publishing Co., Easton, Pa., which is incorporated herein by reference.

As used herein, "sequestration agent" means an agent that enhances localization and/or retention of the *botulinum* toxin to the site of administration.

As used herein, "subject" means a mammal.

B. Albumin.

Endogenous human serum albumin binds native circulating molecules, such as free fatty acids, bilrubin, hormones and zinc. Additionally, circulating human albumin can bind with many pharmaceutical agents which can influence potency, complication rate, clearance, and other pharmacodynamic properties of these agents. Examples include salicylates, sulfisoxazoles, warfarin, phenybutazone, digitoxin, phenytoin, oxacillin, benyzlpenicillin, lasix, indomethacin, diazepam, and quindine among others. Peptides and proteins also are known to bind human serum albumin. Peptide hormones such as gastrin, corticotropin, melatonin are also known to bind human serum albumin.

Several binding sites have been identified and binding has been thought to be non-covalent. Additionally, albumin can non-covalently bind cations that serve as cofactors for enzymatic reactivity of portions of the *botulinum* toxin polypeptide complex. Specifically, zinc is a cofactor for the endopeptidase activity of the *botulinum* toxin light chain which enters the target cells after heavy chain binding to the cell surface protein receptors. Higher quantities of zinc bound to albumin enhance endopeptidase activity. Zinc binding to albumin is dose dependent. Saturation of zinc binding on albumin enhances the denervating effect of *botulinum* toxin.

Albumin, because of larger atomic mass and other protein properties, is physiologically cleared from the injection area by lymph vessel absorption, not blood vessel absorption), a process which a much slower than removal of smaller molecular species. The relevance to *botulinum* toxin pharmaceuticals relate to the role both in maintaining biologic activity by promoting nerve contact and preventing wash out from free neurotoxin release at injection points. DYSPORT®, with its lower albumin concentration, offers less sequestration for the neurotoxin complex, and subsequently, after injected, diffusion away from the targeted anatomic area are results. The clinical effect is a greater regional diffusion of the chemodenervation, which results in increased complications (ptosis, Dyspahgia see Table 2). In order to compensate for this biologic behavior, the clinicians in practice or studies have had to give four to five time as much neurotoxin to achieve the same degree of biologic activity as a higher albumin concentration. With less potent immnuotypes such as *botulinum* toxin type B (MYOBLOC®), larger dose are needed to achieve the same regional bioeffect, hence further diffusion occurs with increased complication rates (see Table 2). Administering more *botulinum* toxin (higher protein load) results in higher immunity rates after repeated injections. (Borodic et al. (1996) *Botulinum* Toxin, Immunology and Problems with Available Materials. *Neurology* 46: 26-29).

MYOBLOC® is formulated at an acidic pH<6.0 which provides for increased stability and stability of the liquid formulation at room temperature. Unfortunately, the acidic pH has an adverse side effect on the structure and probably tissue carrying properties of the human serum albumin in this biologic drug's formulation. At varying pH, the isomerization of albumin can be considerable as well as the tertiary configuration of the albumin protein and physical properties (see Peters (1996) All about Albumin. Academic Press, New York; incorporated herein by reference in its entirety). Alterations in physical properties (via changes in binding of *botulinum* toxin and dynamics of *botulinum* toxin molecular release in tissues) can be used to explain some of the considerable differences in dose requirements comparing BOTOX® and MYOBLOC® in clinical practice. With higher pH, type B formulation, similar histologic effects can be seen with equivalent $LD_{50}$ units (see Borodic et al. (1993) *Botulinum* B Toxin as an Alternative to *Botulinum* A Toxin, A Histologic study. *Ophthalmic Plastic and Reconstructive Surgery* 9(3): 182-190). Although other proteins (e.g. gelatin, lactalbumin, lysozyme), lipids and carbohydrates may serve as effective sequestration agents, albumin, including encapsulated albumin and solid microspheres is the preferred protein sequestration agent, in part, because of its low immunogenicity. Other proteins, polysaccharides, lipids, polymers, gels and hydrogels that are potentially suitable as sequestration agents are disclosed in U.S. Pat. No.: 4,861,627, which is incorporated herein by reference in its entirety. Methods of using and making protein microspheres, including albumin microspheres, are disclosed in U.S. Pat. Nos.: 6,620,617; 6,210,707; 6,100,306; and 5,069,936 which are each incorporated herein by reference in their entirety.

C. Sequestration.

The concept of sequestration has been used by the inventor to explain altered lidocaine toxicity when periocular injections are given in the absence of Wydase. (Troll et al. (1999) Diplopia after cataract surgery using 4% lidocaine in the absence of Wydase™. *Clin Anesth.* 11(7): 615-6). Sequestration, in the absence of Wydase, of injectable lidocaine in this circumstance causes toxicity of myofibrils of the extra-ocular muscles with contraction scarring and damage to extra-ocular movement. The lidocaine example indicates how sequestration from dynamic diffusion of an injectable drug can be important to the drug's basic pharmacology.

There has, however, never been a suggestion or recommendation that albumin can alter regional denervation potency or enhance clinical effects or be used to treat patients not responding to BOTOX®, DYSPORT® or MYOBLOC®. The present invention provides compositions and methods that enhance the clinical effectiveness of *botulinum* toxin pharmaceuticals.

As pointed out in the potency section above, sequestration—the regional containment of chemodervation—is one of the most important properties of the formulations of the present invention. The property in important in enhancing potency, reducing the complication rate from diffusion, and reducing antigenicity of the *botulinum* toxin. Preparations which require higher dosing, that is administration of an increased protein load, are associated with higher rates of immunity (comparing 79-11 orginal Occulinum Batch to current BOTOX® Batch, MYOLOC® compared to BOTOX®). Enhanced sequestration allows for lower protein load, less diffusion, and enhanced biologic effect within the region targeted for treatment. The utility of this improved composition is demonstrated by its therapeutic effectiveness when conventional formulations (eg, BOTOX®, MYOBLOC®) ncurrently in use have failed or given suboptimal results.

D. Dosing of High-Albumin Formulations of *Botulinum* Toxin.

Producing compositions of *botulinum* toxin that require a lower effective amount to treat a particular condition is desired, because the administration of *botulinum* toxin has been associated with the development of immunologic resistance. Consequently, this complication requires increased dosing (higher $LD_{50}$ units) to achieve a therapeutically-effective amount of the *botulinum* toxin.

A composition of Hall-strain-derived *botulinum* toxin was formulated with a specific activity of 20 $LD_{50}$ units/ng toxin and 900 µg human serum albumin to 100 $LD_{50}$ units of *botulinum* toxin(0.11 $LD_{50}$ unit/µg albumin)(US FDA IND 4891). The indication for therapy for this new formulation was aberrant regeneration of the facial nerve with involuntary synkinetic blepharospasm. The study was conducted using between 5 and 15 $LD_{50}$ units of *botulinum* type A toxin formulated with the increased amount of albumin to $LD_{50}$ content.

TABLE 5

Reduction in effective amount of botulinum toxin using high-albumin botulinum toxin compositions.

| Open-Lable Trials | 15 patients each receiving 5-15 $LD_{50}$ units | 100% demonstrated decreased involuntary movement | No ptosis complication |
|---|---|---|---|
| Double-Blind Placebo Controlled Trials | 30 patients (ratio 1:1 treatment/control) each receiving 15 $LD_{50}$ units | 1. Degree of involuntary movements significantly better than controls. 2. Subjective parameters significantly better than controls | No ptosis Complications |

Prior literature has indicated that existing BOTOX® preparations require 20 $LD_{50}$ units to achieve favorable results for this indication. (Borodic et al. (1993) *Botulinum* Toxin for aberrant facial nerve regeneration. Dose response relationships. *Plastic and Reconstructive Surgery*, (91)6: 1042-1045. 1993). Furthermore, there has been a 20% incidence of ptosis (a diffusion complication) associated with the use of *botulinum* toxin for involuntary blepharospasm, based on a 100 patient study on BOTOX® for the treatment of blepharsoapsm and using comparable $LD_{50}$ doses (see new batch approval study from Allergan Pharaceuticals, 1998; incorporated herein by reference in its entirety). Comparing the incidence of this complication in the high-albumin study shown above with the BOTOX® equivalency study (19/99, compared to 0/30, P<0.01, Chi Square), it appears that the high-albumin type A *botulinum* toxin composition required fewer $LD_{50}$ units to achieve acceptable therapeutic results (reduction in effective amount of toxin) and was associated with limited diffusion into the orbit which frequently results in ptosis. The decreased incidence of this complication indicated sequestration of the effects of *botulinum* toxin was enhanced by the higher albumin content.

EXAMPLES

The following Examples serve to further illustrate the present invention and are not to be construed as limiting its scope in any way.

Example 1

Treatment of Blepharospasm

The subject is a 52-year-old female with severe bilateral involuntary blepharospasm. Involuntary movements have prevented her from driving and maintaining gainful employment. BOTOX® was administered by injection on five separate occasions without producing any significant clinical improvement. Surgery was performed to remove a portion of the protractors of eyelid closure (orbicularis oculii). No lasting improvement was observed.

The albumin content of the BOTOX® was altered by adding 5,000 µg human serum albumin to a vial of BOTOX® (100 $LD_{50}$ units). The resulting composition has an albumin concentration of 2,750 µg/cc (0.018 $LD_{50}$/µg albumin). Administration of 60 $LD_{50}$ units of the high-albumin preparation produced a nearly complete resolution of symptoms. The high-albumin concentration was clinically effective even when used in subsequent administrations (4 injection cycles) for over two years.

Example 2

Treatment of Hemifacial Spasm

The subject is a 62-year-old male with a history of bilateral hemifacial spasm. *Botulinum*-toxin therapy using BOTOX® had been ineffective. The spasms impaired his day to day ability to function. Decompression of a facial nerve was attempted surgically on two separate occasions. Both surgeries proved ineffective in attaining acceptable relief of involuntary facial spasms and produced deafness in one ear. The albumin content of the BOTOX® was increased by adding human serum albumin sufficient to achieve a concentration of 5,250 µg/cc (0.00952 $LD_{50}$/µg albumin). Administration of 30 $LD_{50}$ units of the high-albumin preparation proved highly effective and substantially relieved the clinical symptoms.

Example 3

Treatment of Hemifacial Spasm

The subject is a 66-year-old man with right hemifacial spasm. Although he was successfully treated with BOTOX® for 11 years, resistance developed that rendered further injections ineffective. Immunologic-resistance testing, using a remote point injection, demonstrated an absence of circulating antibody. A trial of another *botulinum* toxin formulation, MYOBLOC®, was also ineffective at relieving signs and symptoms.

The albumin content of BOTOX® was increased by adding human serum albumin sufficient to achieve a concentration of 5,250 µg/cc (0.00952 $LD_{50}$/µg albumin). Administration of 40 $LD_{50}$ units of the high-albumin preparation proved highly effective and substantially relieved the clinical symptoms.

Example 4

Treatment of Benign Essential Blepharospasm

The subject is a 72-year-old university president who was diagnosed with benign essential blepharospasm. Four prior injections of the standard BOTOX® preparation failed to achieve any significant improvement. The subject was referred for possible surgical removal of muscle and nerve to weaken muscles necessary for eyelid closure. Instead, a high-albumin preparation of *botulinum* toxin was administered to the usual injections sites that are specific for benign essential blepharospasm. The high-albumin preparation was produced by adding 12,250 µg/cc (0.004 $LD_{50}$/µg albumin). Administration of 60 $LD_{50}$ units of the high-albumin preparation achieved excellent results when the administration of the conventional BOTOX® formulation had failed. Three months after the initial administration of the high-albumin *botulinum* toxin preparation, 40 $LD_{50}$ units of a high-albumin preparation comprising 25,000 µg albumin per 100 $LD_{50}$ units (0.002 $LD_{50}$/µg albumin) were administered and produced greater than 80% relief of the clinical symptoms of blepharospasm.

Example 5

Treatment of Blepharospasm

The subject is a 67-year-old female with blepharospasm that was not responsive to BOTOX® injections. Surgical removal of nerve and muscle failed to provide any relief from involuntary eyelid closures.

Albumin was added to a conventional BOTOX® preparation to produce a high-albumin preparation of *botulinum* toxin with a concentration of 50,250 µg albumin/cc (0.001 $LD_{50}$/µg albumin). Injection of 50 units the high-albumin preparation produced a greater than 50% reduction of symptoms.

Example 6

Treatment of Blepharospasm

The subject is a 77-year-old male who noted tachyphylaxis following repeated *botulinum* toxin injections. Conventional formulations of *botulinum* toxin type B were injected without relief of blepharospasm.

Human serum albumin and 0.5 cc Healon® (hyaloronate) were both added to a 100 $LD_{50}$ units of *botulinum* toxin type A (BOTOX®). The high-albumin preparation produced contained 25,500 µg albumin per 100 $LD_{50}$ units (0.005 $LD_{50}$/µg albumin). Administration of 60 $LD_{50}$ units reduced the clinically-observed involuntary-eyelid contractions.

Example 7

Treatment of Essential Blepharospasm

The subject was a 66-year-old female with essential blepharspasm. Repeated treatment with BOTOX® (type A), using a range between 40 to 300 $LD_{50}$ units, produced no therapeutic benefit. *Botulinum* toxin type B (MYOBLOC®) was administered at a dose of 10,000 $LD_{50}$ units within the periocular region and also failed to produce any relief. Bilateral-facial neurectomy also failed to produce any substantial relief of symptoms. Additional surgical procedures to remove muscles necessary for eyelid closure were similarly ineffective.

Human serum albumin was added to a 100 $LD_{50}$ units of *botulinum* toxin type A (BOTOX®). The high-albumin preparation produced contained 12,750 µg albumin per 100 $LD_{50}$ units (0.00196 $LD_{50}$/µg albumin). Administration of 50 $LD_{50}$ units produced substantial relief of symptoms for a period of three to four months, when other formulations and surgical approaches had failed.

Example 8

Treatment of Severe Chronic Blepharospasm

The subject is an 83-year-old male with severe chronic blepharospasm. The subject had developed ptosis, a diffusion side effect, after repeated treatments with therapeutic doses of conventional *botulinum* toxin formulations. The emergence of ptosis complicated the treatment of this subject by requiring lower doses of *botulinum* toxin. The lower dosing proved less effective.

The patient received an a high-albumin formulation of *botulinum* toxin that was produced by mixing 25,000 µg human serum albumin 100 $LD_{50}$ units of BOTOX®. The high-albumin preparation contained 12,750 µg albumin per cc (0.004 $LD_{50}$/µg albumin). Using the high-albumin preparation, 60-70 $LD_{50}$ units were administered with excellent clinical results and no evidence of ptosis after the therapy. The enhanced sequestration of much higher concentrations of *botulinum* toxin depressed the spread of the neurotoxin into the muscles within the eye socket.

Example 9

Treatment of Essential Blepharospasm

The subject is a 67-year-old woman with essential blepharospasm. The subject underwent treatment with conventional formulations of *botulinum* toxin without relief. In addition, these treatments produced ptosis.

A high-albumin *botulinum* toxin composition (20,000 µg albumin per cc; 0.0025 $LD_{50}$ BOTOX®/µg albumin) was administered to the subject with a resultant clinical improvement of the blepharospasm and no diffusion-related side effects (ptosis).

TABLE 4

Comparison of albumin concentrations used in Examples 1-9 with other formulations.

| Example | Albumin Concentration (μg/cc) | High-Albumin Preparation (LD$_{50}$/μg albumin/cc) | BOTOX ® (LD$_{50}$/μg albumin/cc) | DYSPORT ® (LD$_{50}$/μg albumin/cc) | MYOBLOC ® (LD$_{50}$/μg albumin/cc) |
|---|---|---|---|---|---|
| 1 | 2,750 | 0.0180 | 0.2 | 5 | 10 |
| 2 | 5,250 | 0.0095 | 0.2 | 5 | 10 |
| 3 | 5,250 | 0.0095 | 0.2 | 5 | 10 |
| 4 | 12,500 | 0.0040 | 0.2 | 5 | 10 |
|   | 25,000 | 0.0020 |   |   |   |
| 5 | 50,250 | 0.0001 | 0.2 | 5 | 10 |
| 6* | 10,200 | 0.0050 | 0.2 | 5 | 10 |
| 7 | 25,000 | 0.0020 | 0.2 | 5 | 10 |
| 8 | 12,500 | 0.0040 | 0.2 | 5 | 10 |
| 9 | 20,000 | 0.0025 | 0.2 | 5 | 10 |

LD$_{50}$/mcg albumin/cc for BOTOX ®, DYSPORT ®, MYOBLOC ® given for direct comparison

Example 10

Preparation of a High-Albumin Composition of *Botulinum* Toxin

After quantitizing the biologic effect by dilution of purified *botulinum* toxin, a quantity of albumin is added to the lyophilized material in a quantity sufficient to exceed 500 mg per 100 LD$_{50}$. The increased albumin binds to *botulinum* toxin and enhances sequestration of the injected neurotoxin providing for better saturation of neurotoxin receptors and improved clinical effect.

Example 11

Preparation of a High-Albumin Composition of *Botulinum* Toxin Further Comprising Hyaluronate After quantitizing the biologic effect by dilution of purified *botulinum* toxin, a quantity of albumin is added to the lyophilized material in a quantity sufficient to exceed 500 μg per 100 LD$_{50}$ units. Additionally, another sequestration agent, which further enhances sequestration, is added to keep the *botulinum* neurotoxin from diffusing away from the injections site. Such a sequestration agent includes but is not limited to a diluted solution of sodium hyaluronate. The increased albumin non-covalently binds to *botulinum* toxin and an enhances the sequestration of the neurotoxin providing better saturation of neurotoxin receptors and, consequently, an improved clinical effect.

Example 12

Preparation of a High-Albumin Composition of *Botulinum* Toxin Further Comprising Collagen After quantifying the denervating effect of a *botulinum* neurotoxin by dilution of a purified *botulinum* toxin, albumin is mixed with the lyophilized *botulinum* neurotoxin in a quantity sufficient to exceed 500 μg albumin per 100 LD$_{50}$ units. Additionally, another physical agent, which further enhances sequestration, is added to keep *botulinum* neurotoxin from diffusing away from the injections field. Such an agent would be a diluted mixture of animal or human collagen. The increased albumin non-covalently binds to *botulinum* toxin and an enhances to the sequestration of the neurotoxin proving better saturation of neurotoxin receptors and improved clinical effect.

Example 13

Preparation of a High-Albumin Composition of *Botulinum* Toxin Comprising a Recombinantly-Produced *Botulinum* Toxin-Albumin Fusion Protein

*Botulinum* toxin is produced as a fusion protein with albumin thereby producing an albumin molecule that is covalently linked to a *botulinum* toxin. The fusion protein is tested using the mouse LD$_{50}$ bioassay to determine the effective amount. The regional denervation rabbit ptosis bioassay and mouse hindlimb biossay may be used to confirm the effective amount of a composition comprising the fusion protein. A clinical-dose-escalation study would be further used to confirm and refine effective amount.

Example 14

Testing PURTOX-™ and Other Forms of *Botulinum* Toxin

PURTOX-™, that is *botulinum* type A stabilized with recombinant serum albumin and higher concentrations of albumin will need to be formulated with attention to rSA sources and rSA concentration. Zn++concentration, albumin concentration, and the presence of complex high activity *botulinum* or chromatographically separated pure neurotoxin. Emphasis will be placed on measuring duration of action, changes in critical point. Each preparation will be lyophilized in a low sodium solution, with or without stabilizing sugars.

I claim:

1. A composition comprising a therapeutically effective amount of a *botulinum* toxin, and a human serum albumin, wherein the human serum albumin is present in an amount between 13,000 and 550,000 μg human serum albumin per 100 LD$_{50}$ units *botulinum* toxin.

2. The composition of claim 1, wherein the *botulinum* toxin is selected from the group consisting of: *botulinum* toxin types A, B, C, D, E, F and G.

3. The composition of claim 2, wherein the *botulinum* toxin is *botulinum* toxin type A from Hall strain *Clostridium botulinum*.

4. The composition of claim 1, wherein the *botulinum* toxin comprises fractionated-light-chain *botulinum* toxin.

5. The composition of claim 1, wherein the *botulinum* toxin consists essentially of fractionated light chain *botulinum* toxin.

6. The composition of claim 1, wherein the *botulinum* toxin consists essentially of a mixture of hybrid and chain-translocated forms of *botulinum* toxin.

7. The composition of claim 1, wherein the *botulinum* toxin consists essentially of chimeric forms of *botulinum* toxin.

8. The composition of claim 1, wherein the *botulinum* toxin has a specific activity greater than or equal to 20 $LD_{50}$ units per nanogram *botulinum* toxin.

9. The composition of claim 1 further comprising a pharmaceutically acceptable carrier.

10. The composition of claim 1, wherein the *botulinum* toxin is noncovalently bound to the human serum albumin.

11. The composition of claim 1, wherein the *botulinum* toxin is covalently bound to the human serum albumin.

12. A composition of claim 1 further comprising zinc or a zinc salt.

13. The composition of claim 1, wherein the human serum albumin is present in an amount between 13,000 and 50,500 µg human serum albumin per 100 $LD_{50}$ units *botulinum* toxin.

14. The composition of claim 1, wherein the human serum albumin is present in an amount between 50,500 and 505,000 µg human serum albumin per 100 $LD_{50}$ units *botulinum* toxin.

15. The composition of claim 1, wherein the human serum albumin is formulated as encapsulated microspheres in an amount between 50,500 and 90,500 µg human serum albumin per 100 $LD_{50}$ units *botulinum* toxin.

16. The composition of claim 1, wherein the human serum albumin is formulated as a solid human serum albumin particle.

17. The composition of claim 1, wherein the human serum albumin is recombinantly produced.

18. The composition of claim 1 further comprising one or more additional sequestration agents.

19. A pharmaceutical composition comprising a therapeutically effective amount of a *botulinum* toxin, a human serum albumin and a pharmaceutically acceptable carrier, wherein the human serum albumin is present in an amount between 13,000 and 550,000 µg human serum albumin per 100 $LD_{50}$ units *botulinum* toxin.

20. The pharmaceutical composition of claim 19, wherein the human serum albumin is present in an amount between 13,000 and 50,500 µg human serum albumin per 100 $LD_{50}$ units *botulinum* toxin.

21. The pharmaceutical composition of claim 19, wherein the human serum albumin is present in an amount between 50,500 and 505,000 µg human serum albumin per 100 $LD_{50}$ units *botulinum* toxin.

22. The pharmaceutical composition of claim 19, wherein the human serum albumin is present in an amount between 50,500 and 90,500 µg human serum albumin per 100 $LD_{50}$ units *botulinum* toxin.

23. A composition comprising a therapeutically effective amount of a *botulinum* toxin and a human serum albumin, wherein the human serum albumin is present in an amount between 13,000 and 50,500, between 50,500 and 505,000, or between 50,500 and 90,500, µg human serum albumin per 100 $LD_{50}$ units *botulinum* toxin.

24. A lyophilized pharmaceutical composition comprising a therapeutically effective amount of a *botulinum* toxin, a human serum albumin and a pharmaceutically acceptable carrier, wherein the human serum albumin is present in an amount between 13,000 and 550,000 µg human serum albumin per 100 $LD_{50}$ units *botulinum* toxin.

25. The lyophilized pharmaceutical composition of claim 24, wherein the human serum albumin is present in an amount between 13,000 and 50,500 µg human serum albumin per 100 $LD_{50}$ units *botulinum* toxin.

26. The lyophilized pharmaceutical composition of claim 24, wherein the human serum albumin is present in an amount between 50,500 and 505,000 µg human serum albumin per 100 $LD_{50}$ units *botulinum* toxin.

27. The lyophilized pharmaceutical composition of claim 24, wherein the human serum albumin is present in an amount between 50,500 and 90,500 µg human serum albumin per 100 $LD_{50}$ units *botulinum* toxin.

28. A lyophilized composition comprising a therapeutically effective amount of a *botulinum* toxin and a human serum albumin, wherein the human serum albumin is present in an amount between 13,000 and 50,500, between 50,500 and 505,000, or between 50,500 and 90,500 µg human serum albumin per 100 $LD_{50}$ units *botulinum* toxin.

29. A method of localized denervation in a subject in need thereof, comprising administering a therapeutically effective amount of the composition of claim 1 to the subject to produce localized denervation.

30. The method of claim 29, wherein the subject suffers from a neuromuscular disease associated with increased muscle tone or involuntary movement.

31. The method of claim 30, wherein the neuromuscular disease associated with increased muscle tone with involuntary movement is blepharospasm or torticollis.

32. The method of claim 31, wherein the neuromuscular disease associated with increased muscle tone with involuntary movement is blepharospasm.

33. The method of claim 32, wherein the effective amount is between 10-200 $LD_{50}$ units.

34. The method of claim 31, wherein the neuromuscular disease associated with increased muscle tone with involuntary movement is torticollis.

35. The method of claim 34, wherein the effective amount is between 10 and 3000 $LD_{50}$ units.

36. A method of treating a condition selected from the group consisting of facial wrinkles, rhytides and cosmetic alteration of lip and brow, in a subject in need thereof, comprising administering a therapeutically effective amount of the composition of claim 1 to the subject in order to alleviate at least one symptom of said condition.

37. The method of claim 36, wherein the effective amount is between 2.5 and 400 $LD_{50}$ units.

38. A method of treating human headache disorders in a subject in need thereof, comprising administering a therapeutically effective amount of the composition of claim 1 to the subject in order to alleviate at least one symptom of said human headache disorder.

39. The method of claim 38, wherein the effective amount is between 5 and 1,000 $LD_{50}$ units.

40. A method of treating human migraine headache disorders in a subject in need thereof, comprising administering a therapeutically effective amount of the composition of claim 1 to the subject in order to alleviate at least one symptom of said human migraine headache disorders.

41. The method of claim 40, wherein the effective amount is between 5 and 1,000 $LD_{50}$ units.

42. A method of treating human inflammatory conditions in a subject in need thereof, comprising administering a therapeutically effective amount of the composition of claim 1 to the subject in order to alleviate at least one symptom of said human inflammatory conditions.

43. The method of claim 42, wherein the effective amount is between 5 and 4,000 $LD_{50}$ units.

44. A method of treating myopathic or neuropathic pain in a subject in need thereof, comprising administering a therapeutically effective amount of the composition of claim 1 to the subject in order to alleviate at least one symptom of said myopathic or neuropathic pain.

45. The method of claim 44, wherein the effective amount is between 5 and 4,000 $LD_{50}$ units.

46. A method of treating back pain or arthritic pain in a subject in need thereof, comprising administering a therapeutically effective amount of the composition of claim 1 to the subject in order to alleviate at least one symptom of said back pain or arthritic pain.

47. The method of claim 46, wherein the effective amount is between 5 and 4,000 $LD_{50}$ units.

48. A method of treating gastrointestinal spasm and strictures in a subject in need thereof, comprising administering a therapeutically effective amount of the composition of claim 1 to the subject in order to alleviate at least one symptom of said gastrointestinal spasm and strictures.

49. The method of claim 48, wherein the effective amount is between 5 and 4,000 $LD_{50}$ units.

50. A method of treating a hyperhydrosis syndrome in a subject in need thereof, comprising administering a therapeutically effective amount of the composition of claim 1 to the subject in order to alleviate at least one symptom of said hyperhydrosis syndrome.

51. The method of claim 50, wherein the effective amount is between 5 and 4,000 $LD_{50}$ units.

52. A method of producing the composition of claim 1, comprising mixing human serum albumin and *botulinum* toxin in an amount between 13,000 and 550,000 µg human serum albumin per 100 $LD_{50}$ units *botulinum* toxin.

53. A method of producing the composition of claim 1, comprising freeze drying or flash drying a mixture of a *botulinum* toxin and human serum albumin in an amount between 13,000 and 550,000 µg human serum albumin per 100 $LD_{50}$ units *botulinum* toxin.

54. A method of producing the composition of claim 1, comprising lyophilizing a mixture of a *botulinum* toxin and human serum albumin in an amount between 13,000 and 550,000 µg human serum albumin per 100 $LD_{50}$ units *botulinum* toxin.

55. A composition comprising a therapeutically effective amount of a *botulinum* toxin and a human serum albumin, wherein the human serum albumin is present in an amount between about 13,000 and 25,000 µg human serum albumin per 100 $LD_{50}$ units *botulinum* toxin.

* * * * *